United States Patent [19]

Roberts et al.

[11] Patent Number: 5,440,648
[45] Date of Patent: Aug. 8, 1995

[54] HIGH SPEED DEFECT DETECTION APPARATUS HAVING DEFECT DETECTION CIRCUITS MOUNTED IN THE CAMERA HOUSING

[75] Inventors: James W. Roberts, Guelph, Canada; John G. Elias, Wilmington, Del.; Graham A. Jullien, Tecumseh, Canada

[73] Assignees: Dalsa, Inc., Waterloo, Canada; E. I. Du Pont de Nemours & Company, Wilmington, Del.

[21] Appl. No.: 794,861

[22] Filed: Nov. 19, 1991

[51] Int. Cl.⁶ .................... H04N 7/18; G01N 21/89
[52] U.S. Cl. .......................... 382/8; 356/430; 348/133; 348/88
[58] Field of Search ............. 382/8; 358/101, 106; 356/237, 429, 430; 348/125–128, 133–134, 88; 364/550

[56] References Cited

U.S. PATENT DOCUMENTS

| | | | |
|---|---|---|---|
| 3,920,970 | 11/1975 | Slaker | 356/430 |
| 4,046,536 | 9/1977 | Smithgall, Sr. | 356/430 |
| 4,075,498 | 2/1978 | Takasuka et al. | 250/562 |
| 4,297,676 | 10/1981 | Moriya et al. | 382/53 |
| 4,376,951 | 3/1983 | Miyazawa | 356/430 |
| 4,433,346 | 2/1984 | Stoffel et al. | 358/293 |
| 4,546,444 | 10/1985 | Bullis | 364/550 |
| 4,570,180 | 2/1986 | Baier et al. | 358/106 |
| 4,685,139 | 8/1987 | Masuda et al. | 382/1 |
| 4,752,897 | 6/1988 | Zoeller et al. | 364/550 |
| 4,949,172 | 8/1990 | Hunt et al. | 358/101 |
| 4,949,191 | 8/1990 | Eisen | 358/494 |
| 4,950,911 | 8/1990 | Williams et al. | 250/563 |
| 5,132,791 | 7/1992 | Wertz et al. | 358/101 |
| 5,157,486 | 10/1992 | Baird et al. | 358/101 |
| 5,184,217 | 2/1993 | Doering | 358/106 |

FOREIGN PATENT DOCUMENTS 9114173 9/1991 WIPO.

Primary Examiner—Joseph Mancuso
Assistant Examiner—Larry J. Prikockis
Attorney, Agent, or Firm—Donald W. Marks

[57] ABSTRACT

A defect detection system includes a video camera with defect detection circuits for detecting defects in video signals being outputted by corresponding sections of an array sensor such as a TDI CCD two-dimensional array sensor. Each defect detection circuit includes a subtraction circuit for subtracting a prior stored pixel from an incoming pixel to generate a difference. Comparators compare the difference with positive and negative limits defining an acceptable range of difference values. The prior stored pixel is updated to the succeeding pixel only when the difference value is acceptable. Memories store the defect pixels from the respective detection circuits along with X-coordinates and end of line bits. The memories are sequentially read up to their end of line bits, and the defect pixel values along with coordinates expanded to include section indicating bits are transferred from the camera to further processing facilities.

25 Claims, 10 Drawing Sheets

HIGH SPEED DEFECT DETECTION APPARATUS HAVING DEFECT DETECTION CIRCUITS MOUNTED IN THE CAMERA HOUSING

TECHNICAL FIELD

The present invention relates to defect detection using video cameras, for example, the detection of a defect in a continuous web using a time delay and integration (TDI) charge coupled device (CCD).

BACKGROUND ART

The prior art discloses several defect detection devices and processes using video cameras to produce a video signal which is then analyzed to detect a defect in the objects viewed by the cameras. U.S. patent application Ser. No. 07/493,011 filed Mar. 13, 1990, for WEB INSPECTION SYSTEM by Jean-Louis C. Guay (International Application Publication No. WO 91/14173 published Sep. 19, 1991) discloses the use of a plurality of cameras, each containing a TDI CCD array sensor, arranged in a line across a moving web for generating a plurality of continuous video signals representing images of respective portions of the moving web. These video signals are transmitted from the cameras to respective processing units which analyze the video signals for defects. The analog outputs of the TDI CCD array sensors are converted to streams of binary digital pixel signals either in the camera unit or in the processing units. The digital pixel signals are temporarily stored in computer memories of the processing units until they are analyzed by computers in the processing units to determine the presence of a defect.

One algorithm employed by the computers in the processing units of the above mentioned Guay application sequentially compares each digital pixel value of a line image across a web portion with a dynamically adjustable range. If a present pixel value is outside of the dynamic range but within predetermined ranges above or below the previously tested prior acceptable pixel value then the upper and lower limits of the dynamic range are changed up or down, respectively, by the difference between the present pixel value and the prior pixel value. This compensates for variations in thickness of the web, gradual increases and decreases in pixel values, which are normal and differentiate such normal changes from defects which create sudden changes greater than the predetermined ranges.

One deficiency of prior art defect detecting systems employing video cameras concerns the transmission of analog or digital signals from the cameras to the processing units and the temporary storage of these signals in the processing units. In web defect detection at relatively high resolution, required transmission rates can be up to or higher than thirty-two million bytes or pixels per second per camera. Reliable transmission and handling of a plurality of video signals at such frequencies is difficult and requires relatively expensive facilities. Large (several megabyte) high speed dual ported video memories with facilities to properly address and store incoming signals are required. These memories and their high speed computer processors are relatively complex and expensive. Even with such expensive high speed equipment, there are often unacceptable limitations on inspection rates and/or defect detection resolution.

SUMMARY OF THE INVENTION

In a first aspect, the invention is summarized in a defect detection system having a defect detecting circuit mounted in a camera housing along with an array sensor. An image of an object under test is projected by a lens onto the array sensor. The defect detecting circuit detects pixels of an object defect in a video signal generated by the array sensor. A camera output transmits the detected defect pixels whereby the quantity of pixel values transmitted by the camera output for further processing is less than the quantity of pixel values in the video signal, for example, by a ratio of 1:1000 or less of defect pixels to total pixels.

In a second aspect, the invention is summarized in a defect detection system having a subtraction circuit along with a comparison circuit. A prior pixel value derived from one or more pixels prior to a present pixel value in a video signal from an array sensor is temporarily stored and applied along with the present pixel value to the subtraction circuit which produces a difference between the present pixel value and the stored prior pixel value. The comparison circuit produces a defect signal if the difference exceeds a predetermined value. The subtraction and comparison circuits are operated in real time, with only timing delays for pipelining and synchronization purposes, at high frequencies to enable high resolution detection at high rates.

In a third aspect, the invention is summarized in a defect detection system having a plurality of defect detection circuits connected to a plurality of outputs, respectively, of a two-dimensional CCD array sensor operating in the TDI mode. A plurality of temporary memories, for example conventional first-in, first-out memories (FIFOs), are operated by the respective defect detecting circuits to store the defect pixel values detected in the video signal from the corresponding array output. An output circuit reads the temporary memories and transmits the defect pixel values. Distributing the outputs of a TDI CCD array sensor to corresponding separate defect detecting circuits permits processing of pixels at lower frequencies while providing a greatly increased overall processing rate.

An object of the invention is to provide an economical and effective defect detection system employing an array sensor generating a video signal wherein defects are detected at high resolutions and high rates.

Another object of the invention is to provide a hardware circuit which is simple and small so that it can be readily incorporated in a video camera for detecting object defects in a video signal of the object.

It is also an object of the invention to distribute the pixels from a TDI CCD array sensor in a camera to a plurality of defect detection circuits in the camera so that the video signals can be processed at relatively low frequencies.

One advantage of the invention is that the need for high frequency transmission of video signals from cameras to processing units is eliminated.

Another advantage of the invention is that the computer processing of quantities of video pixel information is greatly reduced.

A further advantage of the invention is that the detection of object defects at high resolutions can be made of objects, such as webs, moving at substantially higher rates than has been previously possible.

An additional feature of the invention is the provision of storing and transferring defect pixel coordinates along with defect pixel values.

A still additional feature of the invention is the provision of expanding initially stored coordinates by bits identifying the section of the object where the defect is found such as by the addition of bits used to multiplex channels in each camera and to multiplex cameras.

It is yet another feature of the invention that there is recognized that reliable defect detection and dynamic adjustment of acceptable range values can be performed by storage of a prior pixel value derived from one or more prior pixels, subtraction of the stored prior pixel value from a present pixel value, comparison of the difference with a predetermined value to determine a defect, and the update of the stored previous pixel value in the absence of the determination of a defect.

A further feature of the invention is the use of half-full, full or other fullness measuring flags of temporary memories or FIFOs to indicate excessive defects and/or to indicate edges of webs under inspection.

A still further feature of the invention is the stopping of storing of defect pixels in a memory when the rate of accumulation of defect pixels exceeds the rate at which the defect pixels are read out.

Yet still a further feature of the invention is the provision for continuing the storage of end of line flags in a memory which has been shut down for excessive accumulation of unread stored defect pixels.

Other objects, advantages and features of the invention will be apparent from the following description of the preferred embodiment and the accompanying drawings.

BRIEF DESCRIPTION OF THE DRAWINGS

FIG. 7 is a time graph of various signals in the circuitry of FIGS. 5 and 6a.

DESCRIPTION OF THE PREFERRED EMBODIMENT

Figure 1:
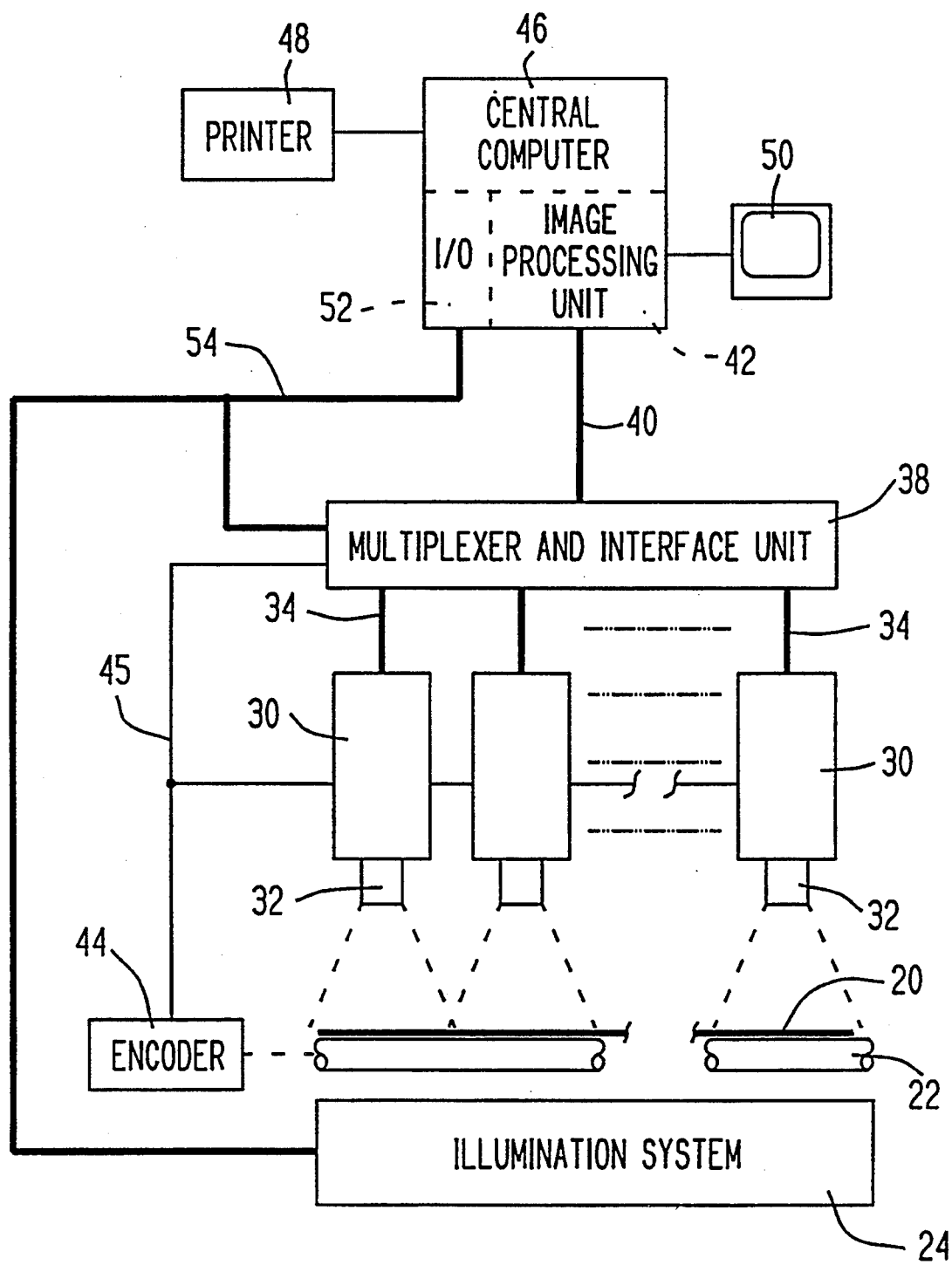
FIG. 1 is a block diagram of a system for detecting defects in a moving web in accordance with the invention.

As shown in FIG. 1, one embodiment of a system and process for detecting defects in an object, such as a moving web or plastic film 20, in accordance with the invention includes a conveyor 22 for directing the moving web through an inspection station having an illumination system 24 and a plurality of video cameras 30 mounted in a line perpendicular to the movement of the web. Lenses 32 of the cameras 30 are selected to view corresponding, slightly overlapping, sections along lines completely across the web. An encoder 44 driven by the conveyor 22 generates pulses at a frequency directly proportional to the speed of the conveyor 22. The encoder pulses are appropriately shaped and amplified and applied over the line 45 to the cameras to synchronize the vertical scan with the web movement.

The cameras 30 themselves analyze the video signals generated from the viewed images to detect defects and produce data on each defect and its relative X-position or coordinate, that is, relative position from one side edge of the section viewed by each camera. Electrical cables 34 connect the cameras 30 to a multiplexer and interface unit 38 which combines the defect data for each transverse image line of the web 20 detected by all the cameras and then suitably passes the defect data over a cable 40 to an image processing unit 42 in a central computer 46. Also the encoder pulses are applied by line 45 to the multiplexer and interface unit 38.

The present system reduces the transfer of video information from the video cameras to image processing units by a factor of 1000 or more. Memory requirements in the image processing units are similarly reduced to that necessary to store and process only the defect data. Requirements for image processing power, such as processing speed or multiple parallel processors, are likewise greatly reduced since the image data being processed in second stage processing is limited to defect data. This results in an economical web inspection system with greatly improved resolution of defects.

The disclosure of U.S. patent application No. 07/493,011 filed Mar. 13, 1990, for WEB INSPECTION SYSTEM by Jean-Louis C. Guay (published as International Application No. WO 91/14173 on 19 Sep. 1991) is incorporated herein in its entirety by reference. The conveyor 22, the illumination system 24, the encoder 44, the computer 46, and the image processing unit 42 are conventional and can be similar to that described in the Guay application. However, defect detection is performed by the cameras 30 and second stage processing 42 is simplified. The unit 42 contains a single processor (not shown) which receives the defect data and suitably processes the data to produce an image of a defect on the monitor 50. The processed defect data is passed by the unit 42 to memory common with the central computer 46 which determines the type of defect in accordance with the algorithms disclosed in the Guay application. The image processing unit 42 also counts the image lines (one end of line flag is passed to the unit 42 for each image line of the web scanned by the cameras) to determine the Y-position, the position along the length of the web, of each defect and passes this position information to the central computer 46.

The central computer 46 from the processed defect data, prints suitable defect information on printer 48, and can store the defect data in magnetic or other mass storage media (not shown). An input/output unit 52 in the central computer 46 operates address and data bus lines 54 connected to the unit 38 as well as to the illumination system 24 for providing control functions and for transmitting and receiving data.

Figure 2:
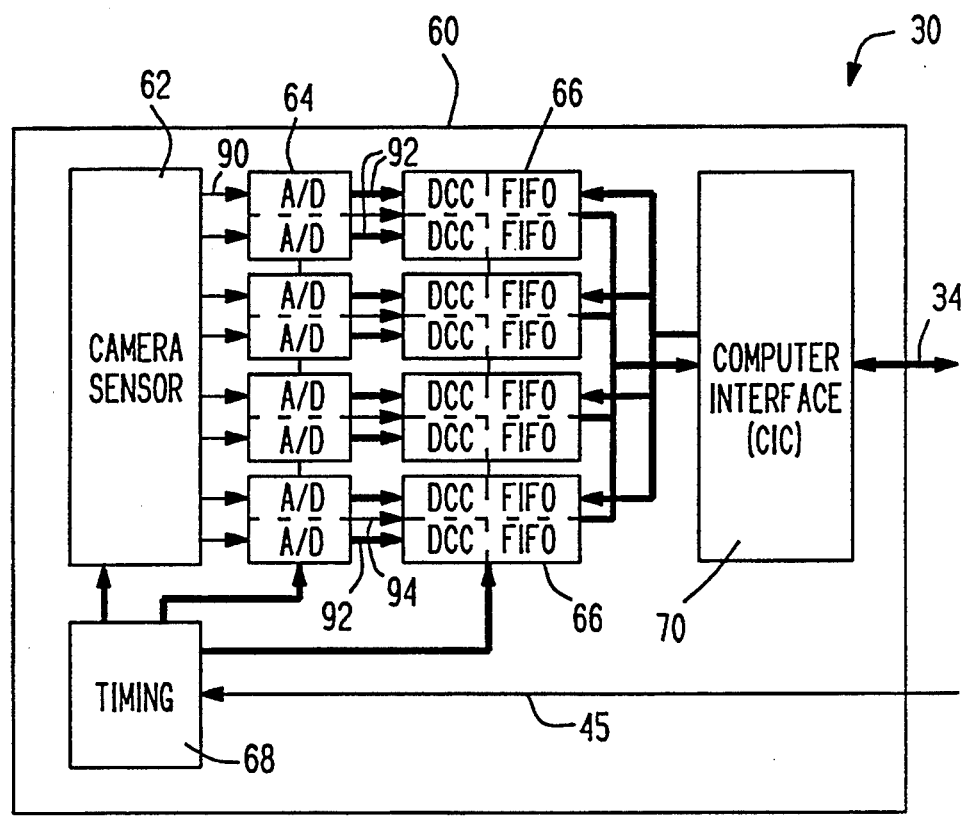
FIG. 2 is a block diagram of circuitry contained within a video camera of the system of FIG. 1.

Each of the cameras 30 includes, as illustrated in FIG. 2, a camera housing 60 in which are mounted a sensor printed circuit card or unit 62, four analog-to-digital conversion printed circuit cards or units 64, four defect detection printed circuit cards or units 66, a timing printed circuit card or unit 68, and a computer interface printed circuit card-or unit 70. The sensor card 62, the analog-to-digital cards 64, and the timing card 68 are commercially available or contain conventional circuitry. The timing circuit 68, synchronized by the pulses on line 45 from encoder 44, FIG. 1, operates and controls the sensor circuit 62, the analog-to-digital circuits 64 and the defect detection circuits 66.

Figure 3:
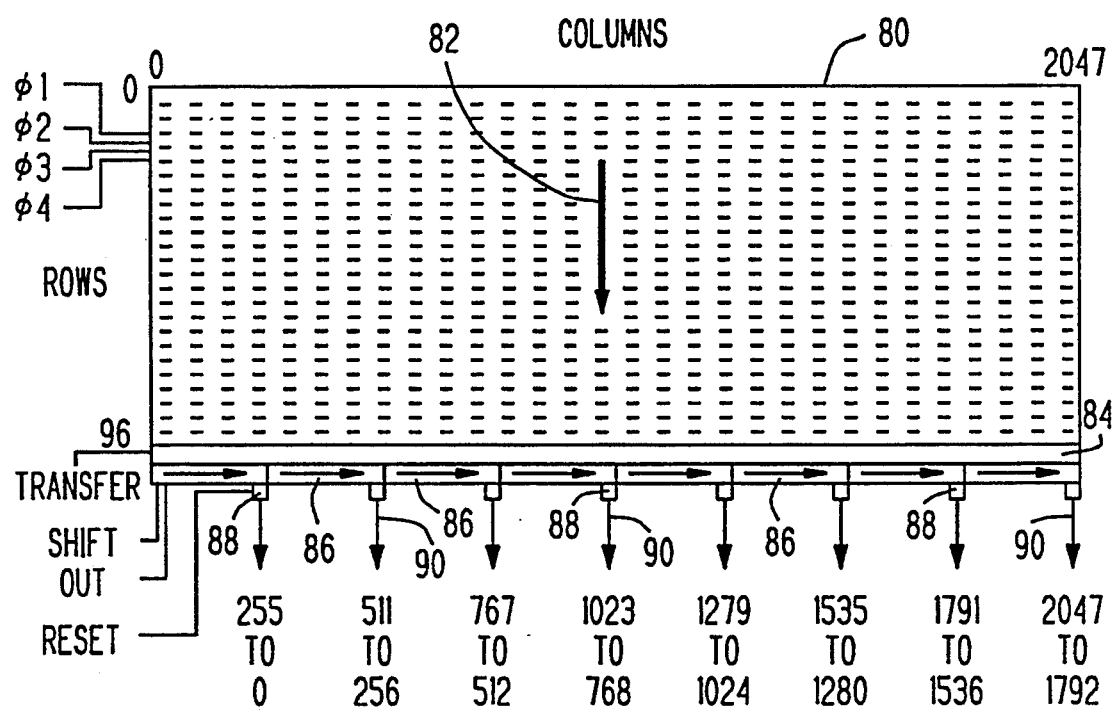
FIG. 3 is diagrammatic view of a TDI CCD two-dimensional array sensor in the circuit of FIG. 2.

The sensor card 62 includes a conventional TDI CCD two-dimensional array sensor 80, FIG. 3, which has an array of sensing photosites arranged in columns 0 through 2047 and rows 0 through 96 upon which an image of a corresponding section of the moving web is projected by the camera lens. An electrical charge is generated and accumulated at each photosite proportional to the quantity of photons impinging on each photosite. Phase signals $\phi 1$, $\phi 2$, $\phi 3$ and $\phi 4$ generated in synchronism with encoder pulses on line 45, FIG. 2, simultaneously shift the rows of electrical charges in the direction of arrow 82 so that the charges move in correspondence to the movement of the image over the sensor array. In this manner the charge for each image pixel is integrated or accumulated in the array as each image pixel moves in its corresponding column from row 0 to row 96. When the integrated charges reach the row 96, the charges are transferred by transfer gates 84 to shift registers 86. The shift registers 86 are operated in parallel by high frequency shift out signals to serially output charges between the shifts of rows of charges. The shift out signals serially transfer the charges in the shift registers 86 to respective diffusion output regions 88 from which video analog voltage outputs 90 are derived. Reset signals restore the diffusion regions between output pixel voltages.

Each of the eight outputs 90 corresponds to a respective section of each line of pixel voltages being outputted, such as pixels 255 to 0, 511 to 256, etc. Thus the pixels of each line of an image portion viewed by a camera are distributed to the eight outputs 90. The pixels of each section are outputted in reverse order so that the time displacement of each output pixel corresponds inversely to the X-position of the image pixel in the corresponding image section. Although the present sensor 80 outputs the pixels from each line image section in reverse order, the sensor 80 could be a sensor designed to output the pixels in forward order, i.e. from 0 or 255, 256 to 511, etc.

Referring back to FIG. 2, a pair of the outputs 90 are applied to each analog-to-digital circuit card 64 which contains two conventional analog-to-digital conversion circuits to generate respective output streams 92 of eight-bit parallel digital pixel signals which are applied to inputs on a respective defect detection circuit card 66. Clock or strobe signals on lines 94 between the circuit cards 64 and 66 are also supplied to the defect detection circuits.

Each of the defect detection circuit cards 66 contain two parallel circuits or channels for detecting defects in the respective digital pixel streams 92. Each of these detection circuits include a data compression circuit (DCC) and a first-in first-out memory (FIFO). These circuits serve to eliminate non-relevant background pixels from the video digital streams except that one background pixel value is saved and transmitted along with each group of defect pixels, and one initial background pixel value is saved and transmitted along with an end of line flag (EOL) at the end of each scan line.

Figure 4:
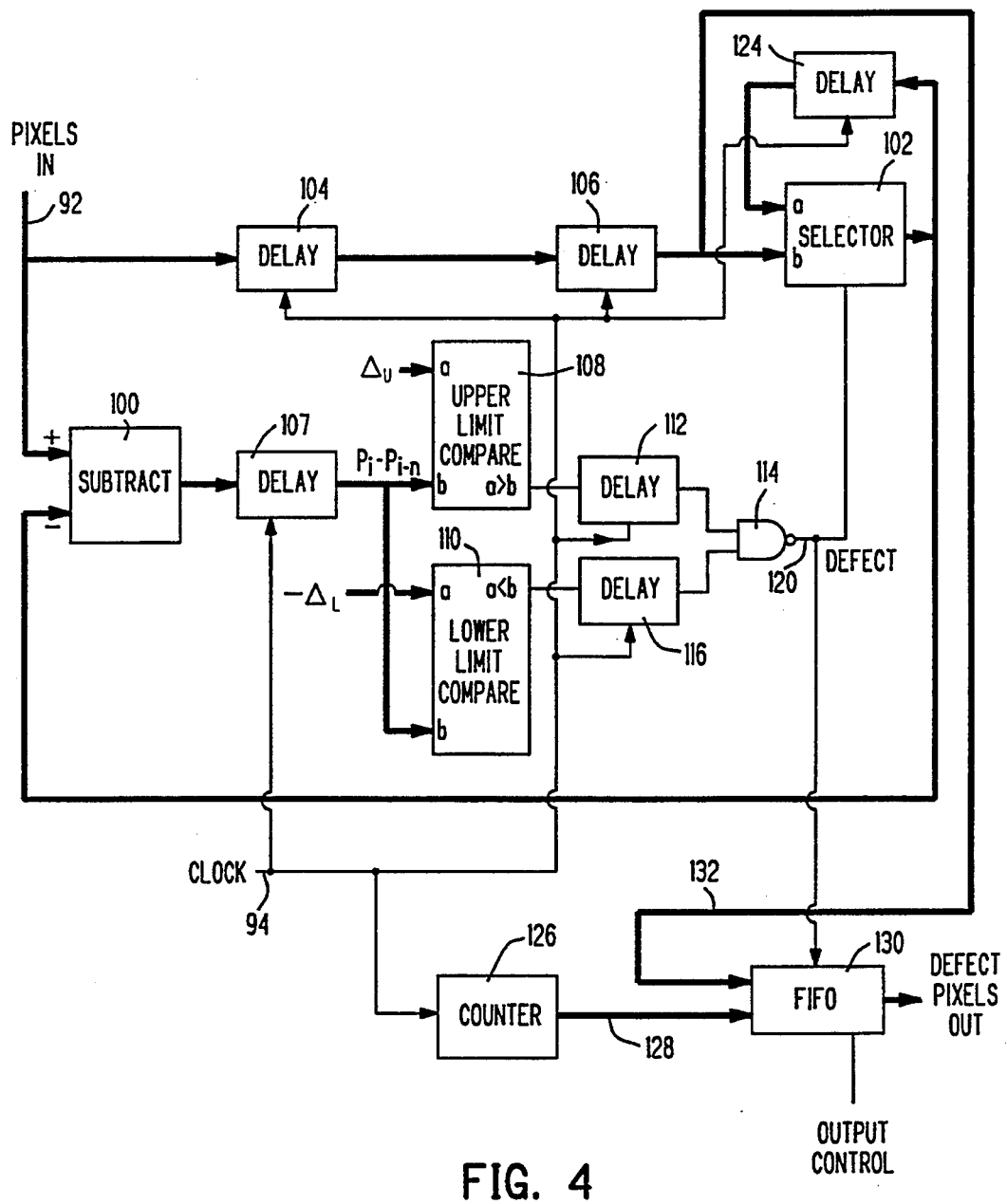
FIG. 4 is a functional block diagram of a defect detection circuit employed in the circuit of FIG. 2.

The function of the DCC and FIFO circuits is illustrated in FIG. 4 wherein digital pixel stream 92 is applied to one input of subtraction circuit 100 which has the digital output of a selector 102 applied to the second input of the subtraction circuit. One input of the selector is connected by two serially connected delay circuits 104 and 106 to the incoming digital pixel stream 92 to normally apply a prior digital pixel value to the second input of the subtraction circuit. The difference output $(P_i-P_{i-n})$ of the subtraction circuit 100, after passing through a delay 107, is compared with a predetermined upper difference limit value $\Delta_U$ in a comparator 108 and with a predetermined lower difference limit value $-\Delta_L$ in a comparator 110 wherein $P_i$ is the present digital pixel value and $P_{i-n}$ is a prior digital pixel value. The greater than output $(-\Delta_U>(P_i-P_{i-n}))$ of the comparator 108 is connected by a delay circuit 112 to one input of a NAND gate 114 while the less than output $(-\Delta_L<(P_i-P_{i-n}))$ of the comparator 110 is connected by a delay circuit 116 to the second input of the NAND gate 114. In the absence of a defect, the greater than output of comparator 108 and the less than output of comparator 110 are both true (high) which generates a false (low) from gate 114 on DEFECT line 120. The DEFECT line 120 is connected to the control input of selector 102 to select the input from delay circuit 106 to normally pass the digital pixel $P_{i-n}$ to the subtraction circuit in the absence of a defect.

The delays 106, 107, 112 and 116 are included to provide pipelining and maximum throughput of the circuit. The circuit would function properly without these delays 106, 107, 112 and 116 but would have a lower maximum operating frequency.

The subtraction circuit 100, the comparators 108 and 110, and the NAND gate 114 provide a determination of whether the pixel value is within a dynamic acceptable range $(P_{i-n}-\Delta_L)$ to $(P_{i-n}+\Delta_U)$. The acceptable range is updated or dynamically changed by changing the value $P_{i-n}$ to track normal gradual pixel changes.

A delay circuit 124 is connected between the output and the other input of the selector 102. When a pixel or pixels of a defect on digital input 92 are presented to subtraction circuit 100, the DEFECT line 120, after the appropriate delay, goes true (high) to operate selector 102 to supply the output of the delay circuit 124 to the second input of the subtraction circuit 100. Thus during a defect, the subtraction circuit subtracts a prior normal digital pixel value stored in the delay 124 from the incoming pixel values. The selector 102 during a defect signal does not update the comparison or reference pixel value to a new $P_{i-n}$ from delay 106 until the defect pixels are passed. It is noted that in the case of a defect, n in $P_{i-n}$ is increased dynamically by the number of clock pulses required to pass the defect and is returned to its initial value after the defect passes.

The clock or strobe input 94 operates the delay circuits 104, 106, 112, 116 and 124 to produce the proper synchronization of the circuit. Also the clock 94 steps a count-down counter 126 which is operated to indicate the relative X-position or coordinate of the pixel under test with respect to the beginning of the segment of line image being examined for defects; if the sensor 80 is selected to output the pixels in forward order, the counter 126 is operated to count up to indicate the relative X-coordinate. When the DEFECT line 120 goes true the input control of FIFO 130 is operated to store the defect pixel value and its X-coordinate from counter 126 in the FIFO. The stored defect pixel data is subsequently read out of the FIFOs by the computer interface circuit (CIC) 70, FIG. 2, and transferred to the corresponding secondary processing unit for further analysis.

Figure 5:
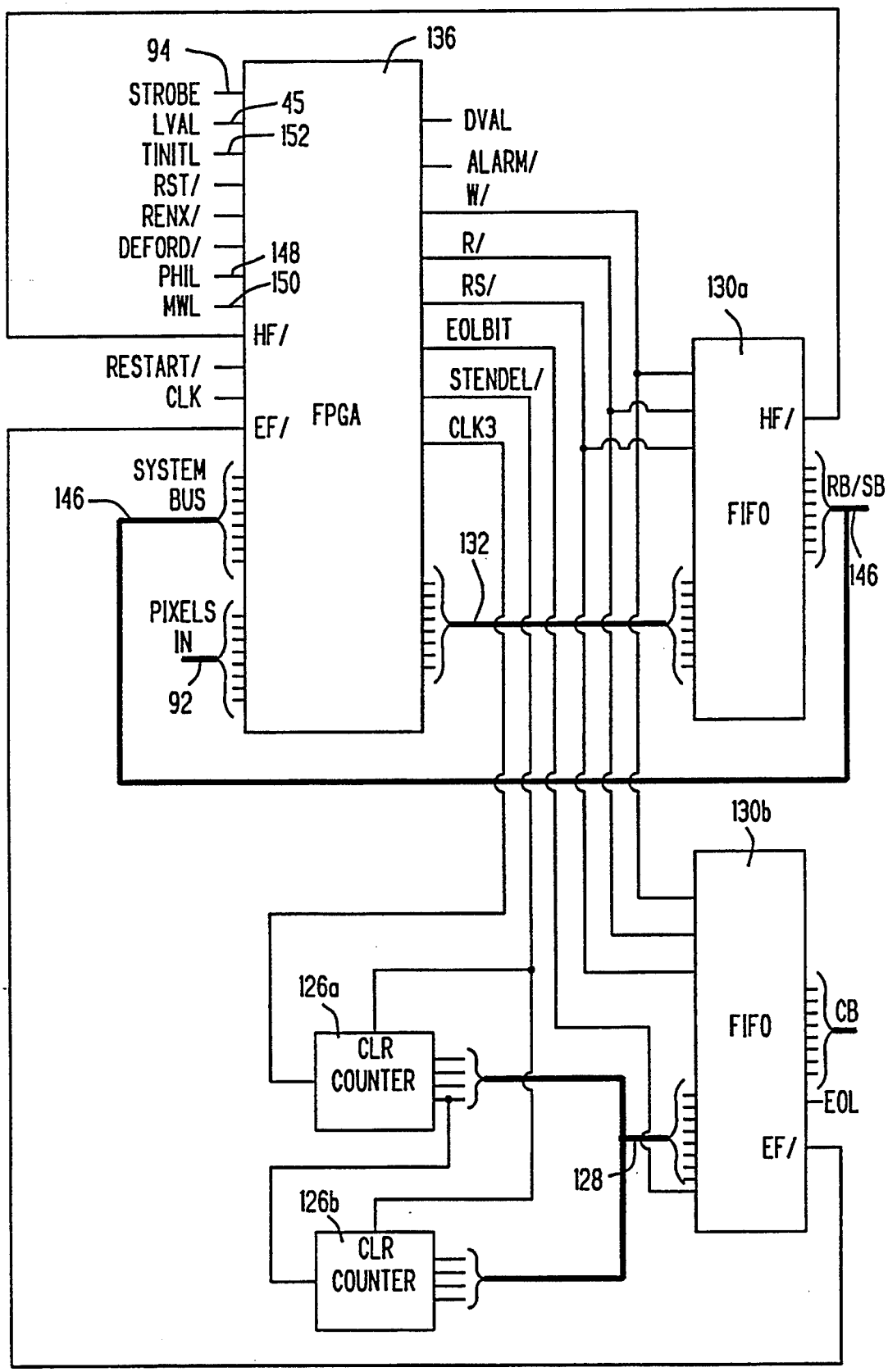
FIG. 5 is a detailed block diagram of electrical circuitry forming a defect detection circuit for one channel of the circuit of FIG. 2.

The circuitry forming the DCC and FIFO for one channel on one of the cards 66 is shown in FIG. 5 and includes a field programmable gate array chip (FPGA) 136, two nine-bit conventional FIFO chips 130a and 130b, and two four-bit conventional counter chips 126a and 126b. Conveniently, each of the cards 66 are manufactured with identical circuitry and have jumpers (not shown) for enabling channel selection in a conventional manner during camera assembly.

Figure 6A:
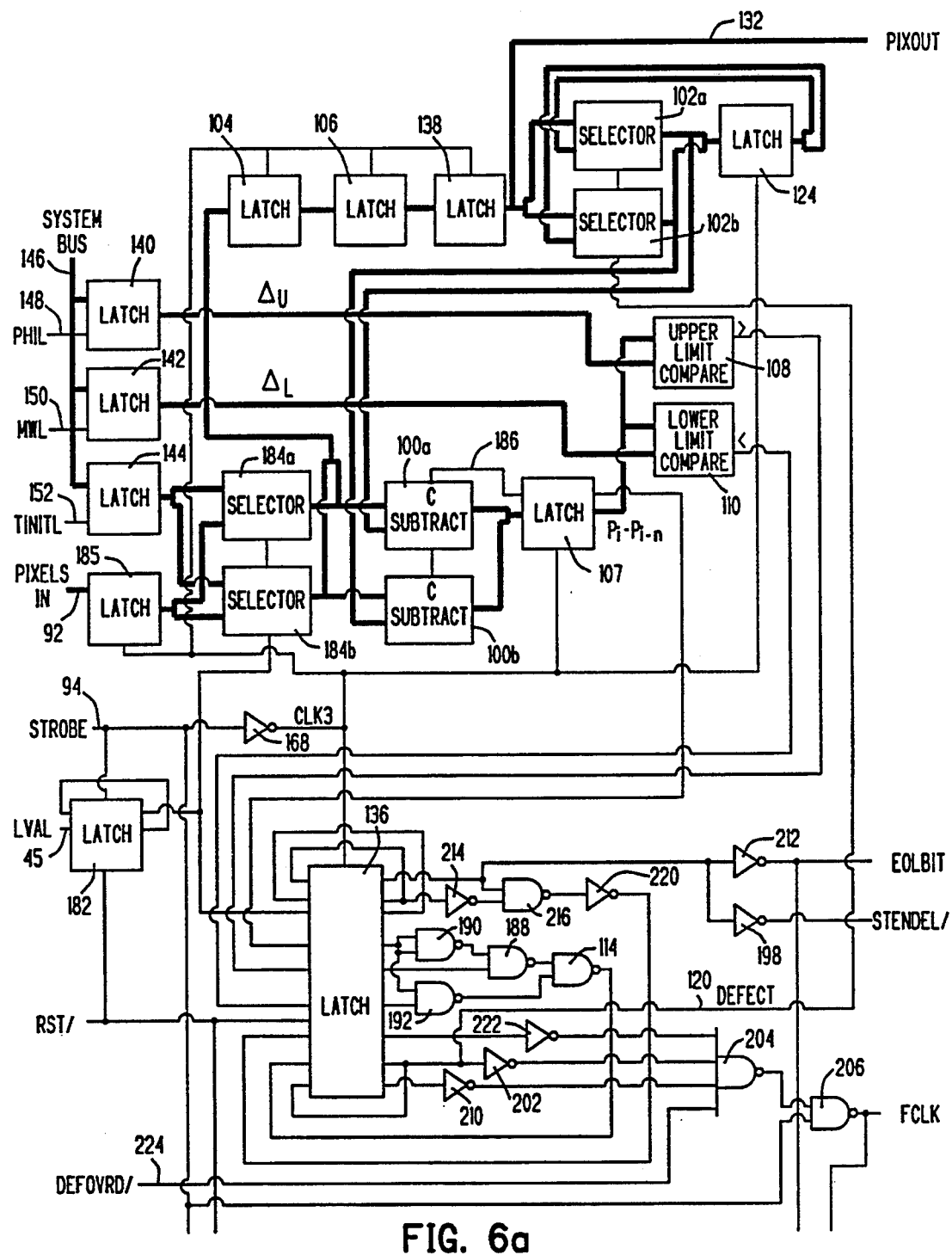
FIGS. 6a and 6b, when joined with FIG. 6a on top and FIG. 6b on bottom, form a detailed electrical block diagram of circuitry incorporated in a field programmable gate array unit (FPGA) in the circuit of FIG. 5.
Figure 6B:
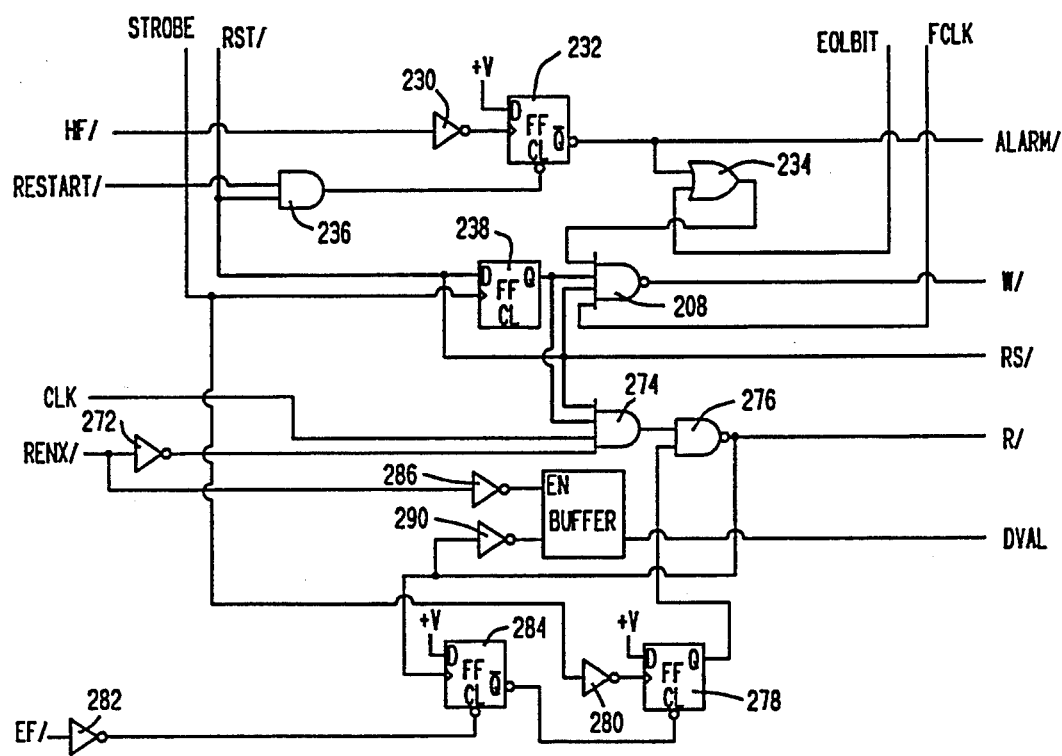

FIGS. 6a and 6b show a hardware design of suitable DCC circuitry for being incorporated in a field programmable gate array (FPGA) such as available from Altera Corporation, San Jose, Calif., USA. Because of design limitations and/or optimizing design decisions, the subtraction circuit 100 of FIG. 4 is incorporated in a pair of cascaded four-bit ALU circuits 100a and 100b (still labeled as subtract circuits) in FIG. 6a, and the selector circuit 102 of FIG. 4 is incorporated is a pair of four-bit multiplexer circuits 102a and 102b (still labeled as selectors) formed as Boolean units. The delays 104, 106, 107 and 124 of FIG. 4 are formed by eight-bit latch circuits 104, 106, 107 and 124 of FIG. 6a. The delays 112 and 116 of FIG. 4 are incorporated in respective stages of a nine-bit latch circuit 136 in FIG. 6a. An additional delay is interposed between the output of the NAND gate 114 and the DEFECT signal line 120 by a stage of the latch 136 while an additional eight-bit delay latch 138 is interposed between the output of latch 106 and the inputs of selectors 102a and 102b.

Eight-bit latches 140, 142 and 144 have data inputs connected to a system bus 146 which shares lines RB/SB with the eight-bit gray value portion of output data from the FIFO 130a to the computer interface circuit 70 of FIG. 2. Clock inputs of latches 140, 142 and 144 are connected to respective control lines 148 (PHIL), 150 (MWL) and 152 (TINITL) from the computer interface circuit for storing operating values transferred over the system bus SB from the central computer 46, FIG. 1, through the interface unit 38. The value $\Delta_U$ is received and applied by latch 140 to the compare circuit 108. The value $\Delta_L$ is received and applied by latch circuit 142 to the compare circuit 110. An initial pixel value is received in the latch 144 for flushing prior pixel values in the pipeline and for presenting the initial prior pixel value upon start of the detection of line pixel values. The strobe input 94 is inverted by an inverter 168 to form a clock signal CLK3 which operates various latches in FIG. 6a and operates the counter 126a in FIG. 5.

An encoder pulse input 45 (LVAL) from the timing circuit 68 of FIG. 2 is high (see also FIG. 7) when data on pixel input 92 is the actual digital value of a pixel in a video line being outputted from the analog-to-dig converter units 64. The input LVAL is delayed by two stages of a latch circuit 182 operated by the strobe 94 to operate four-bit selectors 184a and 184b which have first inputs connected to the output of the latch 144 and second inputs connected to an output of an eight-bit latch 185 receiving the input pixels 92. The outputs of the selectors 184a and 184b are connected to the minuend inputs of the subtracting circuits 100a and 100b as well as to the input of latch 104. The subtrahend inputs of the subtracting circuits 100a and 100b are connected to the outputs of the selectors 102a and 102b.

The carry or borrow output 186 of the unit 100a is a ninth bit delayed by the latch 107 and a stage of latch 136 to enable a NAND gate 188 via inverter 190 when the carry signal 186 is low indicating that the $P_{i-n}$ minuend $P_{i-n}$ is equal to or greater than the subtrahend and to enable gate 192 when the carry signal is high indicating a negative difference value. This gating is necessary since negative differences outputted from subtract circuits 100a and 100b are twos complements. When the gate 188 is enabled, the greater than output of the upper limit comparator 108 is passed through a stage of the latch 136 and the gate 188 so that the gate 114 passes the result from the upper limit comparator as the defect signal 120. When the gate 192 is enabled, the less than output of the lower limit comparator 110 is passed through the latch 136 and the gate 192 so that the gate 114 passes the result from the lower limit comparator as the defect signal 120.

The use of a prior pixel value as a reference value for a dynamic range of acceptable values in the circuit of FIGS. 5 and 6a is based upon a finding that normal pixel values vary very slowly in plastic films being analyzed. However, different testing conditions, such as larger induced noise levels, could cause excessive errors in defect detection. Under such different conditions, errors in defect detection can be reduced by the employment of a pixel averaging circuit (not shown) or a filtering circuit (not shown) such as a finite impulse response (FIR) filter (not shown) or an infinite impulse response (IIR) filter (not shown) in series with latches 104 and 106 so that the prior pixel value presented to the selector 102 is an average or filtered value derived from one or more prior pixels.

The delayed LVAL signal from latch 182 is further delayed by three stages of latch 136 and applied by inverter 198 as the signal STENDEL/ to the CLR input of the counters 126a and 126b. In the absence of incoming pixels, i.e. LVAL being low, the counters 126a and 126b are reset to zero. When the pixels are outputted from the sensor in reverse order as described herein, the outputs of the counters 126a and 126b are to be inverted to correspond to the X-position of the incoming pixels; due to hardware limitations, this inversion is performed by software in the image processing unit 42 rather than by count-down counters or inverters in the camera. If the incoming pixels were not reversed, such inversion or count-down counter is unnecessary.

The defect signal 120 is applied by an inverter 202 to one input of a NAND gate 204 which enables a NAND gate 206 to pass the strobe signal 94 to output FCLK. The output FCLK is applied to one input of a NAND gate 208, FIG. 6b, which, when enabled, generates a write signal W/ to operate the FIFOs 130a and 130b, FIG. 5, to store the value of the defect pixel on bus 132 from latch 138 in FPGA 136 and to store the position or X-coordinate on bus 128 from the counters 126a and 126b. Additionally the defect signal is further delayed by another stage of the latch 136 and applied by an inverter 210 to a second input of NAND gate 204 so that the position and value of the first normal pixel following a series of one or more defect pixels is stored in the FIFOs 130a and 130b. The value and position of this normal pixel are transmitted along with the defect pixel data from the cameras to the second stage processing apparatus to enable the further processing of this data.

The thrice delayed signal LVAL from latch 136 is applied by inverter 212 to an output EOLBIT which is applied as one bit input to the FIFO 130b. The twice delayed LVAL signal from latch 136 is inverted by an inverter 214 and applied to one input of a NAND gate 216 which receives the thrice delayed LVAL signal on its other input. The output of the NAND gate 216 is inverted by an inverter 220, delayed by another stage in latch 136, inverted by an inverter 222, and applied to a third input of NAND gate 204 to store a high EOLBIT signal in the FIFO 130b along with the position zero and the initial value from latch 144 after the last incoming pixel value of a line section has been tested for a defect value. During the evaluation of pixels in a line section, the EOLBIT signal is low so that the corresponding FIFO stored bit in each defect pixel record is low.

The computer interface has a defect override line 224 (DEFOVRD/) connected to a fourth input of the NAND gate 204 to output all the pixels passing to output 132. The line 224 is normally high and is rendered low when it is desired to look at pixels or values other than the defect pixels, background pixels, and end of line bits normally stored in the FIFOs.

Figure 7:
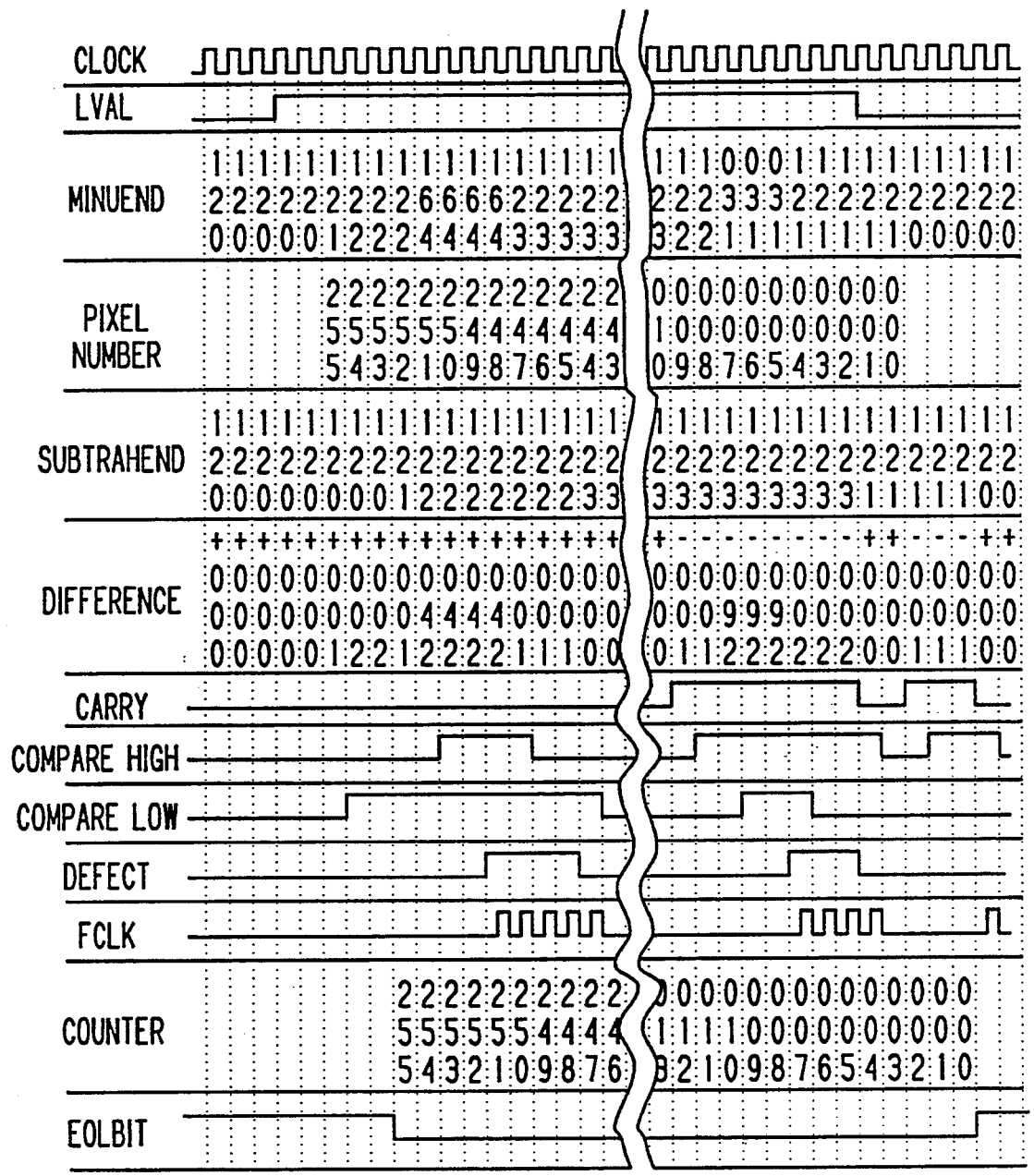

An example of operation of the circuit of FIG. 6a is illustrated in FIG. 7. The upper waveform (CLOCK) represents the clock signal CLK3 distributed to various portions of the circuit. It is noted that FIG. 7 illustrates the relative timing of various circuit portions, but FIG. 7 is not in sufficient detail to accurately reflect the relative phase shift inherent in the various circuit components of FIG. 6a. The values MINUEND, SUBTRAHEND, DIFFERENCE and COUNTER are set forth in FIG. 7 as decimal numbers, but in the circuit of FIG. 6a these values are presented as parallel eight-bit binary signals. The row DIFFERENCE contains negative decimal numbers, but in the circuitry of FIG. 6a, negative numbers are the twos complement. The row PIXEL NUMBER in FIG. 7 is inserted for reference purposes to identify the MINUEND image pixels and does not represent any values or signals in FIG. 6a. The COUNTER values represent inverted outputs of counters 126a and 126b of FIG. 5.

While LVAL is low, the initial value, one hundred twenty, stored in latch 144 is applied to the minuend inputs of the subtracting circuits 100a and 100b. Since this value will have been flushed through the latches 104, 106 and 138, the subtrahend is also equal to one hundred twenty and the difference is zero. When LVAL goes high indicating that line pixel values are now being applied to latch 185, the selectors 184a and 184b, after a delay, are operated to apply the incoming pixels to the minuend input of the subtracting circuits 100a and 100b. The first line image pixel, number 255, has a value of one hundred twenty-one, while pixels, numbers 254-252, have values of one hundred twenty-two. These values do not appear in the subtrahend until three clock periods later so difference values of plus one and plus two are generated. The value $\Delta_U$ is set at plus three and the value $\Delta_L$ is set at minus three, i.e. 11111101. Since plus two is not greater than plus three, the compare high output of the upper limit comparator 108 remains low. The compare low output of lower limit comparator 110 does go high, but the carry signal on line 186 remains low so the gate 192 is disabled to block passage of the compare low signal to the defect gate 114.

Pixels, numbers 251-248, are defect pixels with values of one hundred sixty-four. Since the difference of plus forty-two is greater than plus three, the compare high output goes high to produce a high defect signal DEFECT. The high defect signal enables the FCLK signal so that the values of pixels 251-248 along with the pixel X-positions from counters 126a and 126b are stored in the FIFOs 130a and 130b. The high defect signal DEFECT on line 120 also operates the selectors 102a and 192b to prevent the defect values, one hundred sixty-four, being applied to the subtrahend. Rather the subtrahend is held at the last subtrahend value stored in latch 124 before the defect signal, i.e. one hundred twenty-two. In the clock period following the end of the defect signal DEFECT, the next normal pixel value and its coordinate are stored in the FIFOs due to the delayed defect signal through inverter 210 to operate gate 204.

Pixels, numbers 9 and 8, have values, one hundred twenty-two, applied to the minuend input which are less than the value, one hundred twenty-three, applied from a prior normal pixel to the subtrahend input. This results in a difference of negative one (11111111) which is not less than the value $\Delta_L$ (11111101) so the compare low output of the lower limit comparator 110 is low. The carry signal is high to disable the gate 188 and to prevent the compare high signal from operating the defect gate 114.

Pixels, numbers 7-5, have values, thirty-one, which produce a difference of negative ninety-two (10100100) which is less than negative three (11111101) to produce a high defect signal DEFECT on line 120. This results in the storing of the values of pixels, numbers 7-4, along with their coordinates in the FIFOs.

When LVAL goes low marking the end of line pixel input, the coincidence of inverted twice delayed LVAL and thrice delayed LVAL operates gate 216 which after a further delay operates gate 204 to produce a pulse in FCLK to store a further record in the FIFOs 130a and 130b. This record contains the high EOLBIT signal to indicate the end of a line. Also this end of line record contains the initial value from latch 144 which will have been flushed through the pipeline.

The FIFOs 130a and 130b of FIG. 5 have outputs HF/ and EF/ which, when low, indicate over half full and empty conditions, respectively, of the FIFOs. The half full signal HF/ is applied by inverter 230 in FIG. 6b to the clock input of a flip-flop 232. The inverted output of the flip-flop 232 generates an output ALARM/ which is high in the absence of the half full signal and is applied by OR gate 234 to an input of the NAND gate 208. When the half full signal HF/ goes low, the flip-flop 232 is operated to render the output ALARM/ low and disable the gate 208. This prevents data of any further defect signals from being written to the FIFOs of the channel producing the alarm signal. However, the end of line signal EOLBIT is applied to the second input of OR gate 234 so that end of line records continue to be written in the FIFOs. The size of the FIFOs 130a and 130b, for example 2048×9 bit FIFOs, is selected to allow storage of a normal maximum number of defects. When defect pixels are detected at a rate greater than the rate at which the pixels are read out, the FIFOs over a period of time become half full to shut down storage of further defect pixels.

The alarm signals indicating shutdown of a channel have an additional function, namely that of indicating the edge of the web being examined for defects. The channels viewing image sections outside or straddling the edges of the web detect large numbers of defect pixels which quickly produce an alarm signal and shut down the defect detection of those channels. The alarm signal can be turned off by either a RESTART/ signal or a RST/ signal applied to a respective input of an AND gate 236 which clears the flip-flop 232. The RST/ signal also resets the latches 182 and 183 in FIG. 6a, operates a flip-flop 238 in FIG. 6b to disable the write signal W/ for the remaining portion of a strobe pulse cycle after termination of the RST/ signal, and is passed of line RS/ to reset the FIFOs 130a and 130b of FIG. 5.

Figure 8:
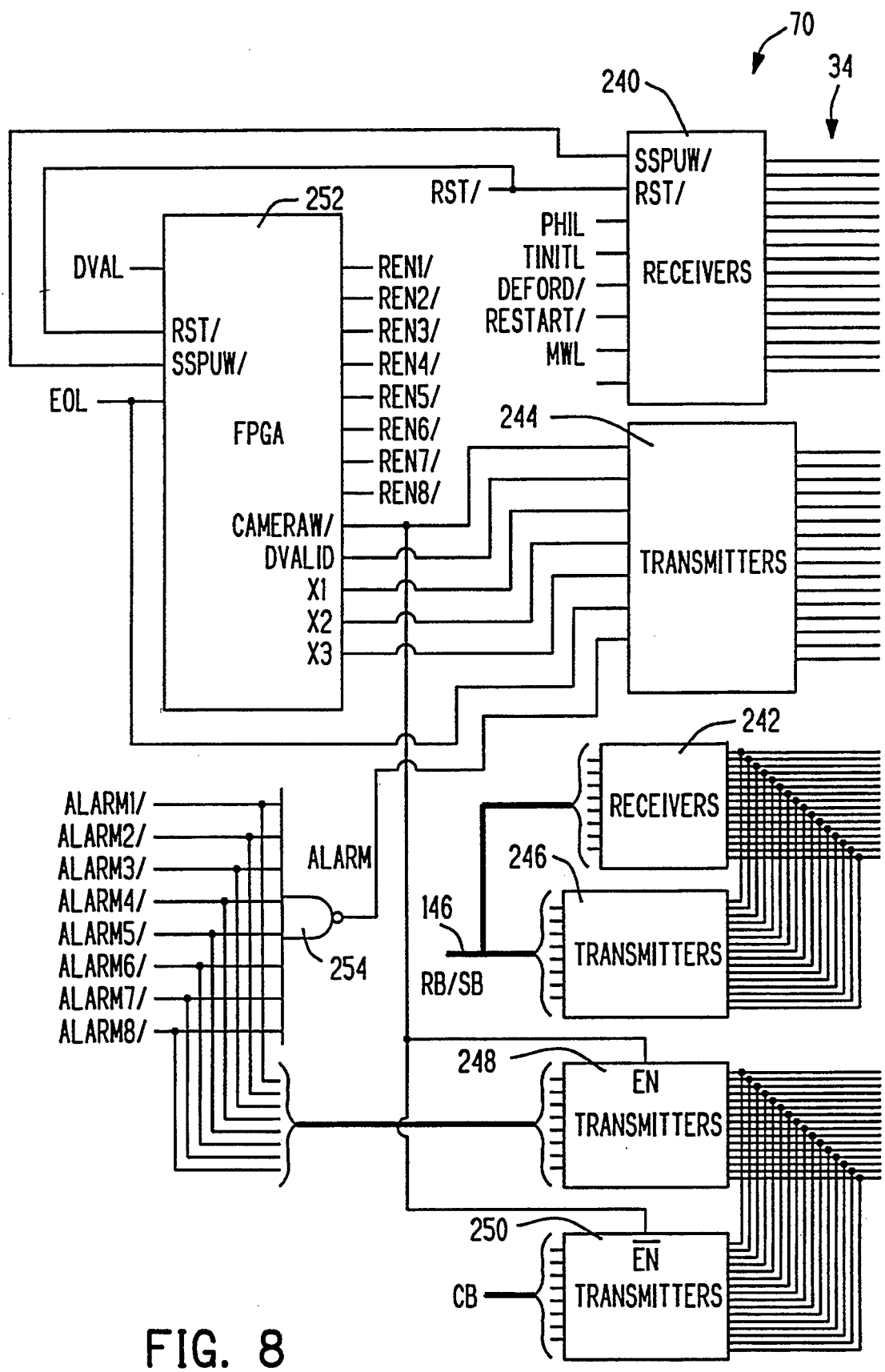
FIG. 8 is a detailed block diagram of camera output circuitry in the circuit of FIG. 2.

As illustrated in FIG. 2, the computer interface circuit 70, connects the defect detection circuits 66 to the cable 34 to the multiplexer and interface unit 38, FIG. 1. The circuit 70, as shown in FIG. 8, includes RS-422 type receivers 240 and 242 and RS-422 type transmitters 244, 246, 248 and 250 connected to lines in the cable 34. The receivers 240 receive control signals RST/, PHIL, TINITL, DEFOVRD/, RESTART/, and MWL which are passed to the defect detection circuits 66, and receive a control signal SSPUW/ which, along with the signal RST/, is applied to a FPGA 252 controlling the multiplexed reading of the eight defect detection channels in circuits 66. The receivers 242 receive eight-bit data signals which are passed to the system bus (RB/SB) 146 when SSPUW/ is low and CAMERAW/ is high, and the transmitters 246 transmit signals on bus RB/SB 146 from FIFO 130a when SSPUW/ is high and CAMERAW/ is low. Transmitters 244 transmit control signals CAMERAW/ and DVALID from the FPGA 252 along with an alarm data signal ALARM from NAND gate 254 which has inputs connected to all eight of the alarm outputs of the defect detection circuits. Additionally the transmitters 244 transmit the end of line bit EOL and three bits X1, X2 and X3 which identify which one of the eight data detection channels is being read. The X-coordinate data in the defect records being read are transmitted from bus CB connected to the data outputs of the FIFOs 130b in the eight defect detection circuits when the signal CAMERAW/ is low. When CAMERAW/ is high, the transmitters 248 pass the alarm signals ALARM-1/-ALARM8/ from the eight defect detection channels to the RS-422 lines in cable 34 shared with the outputs of transmitters 250.

Figure 9:
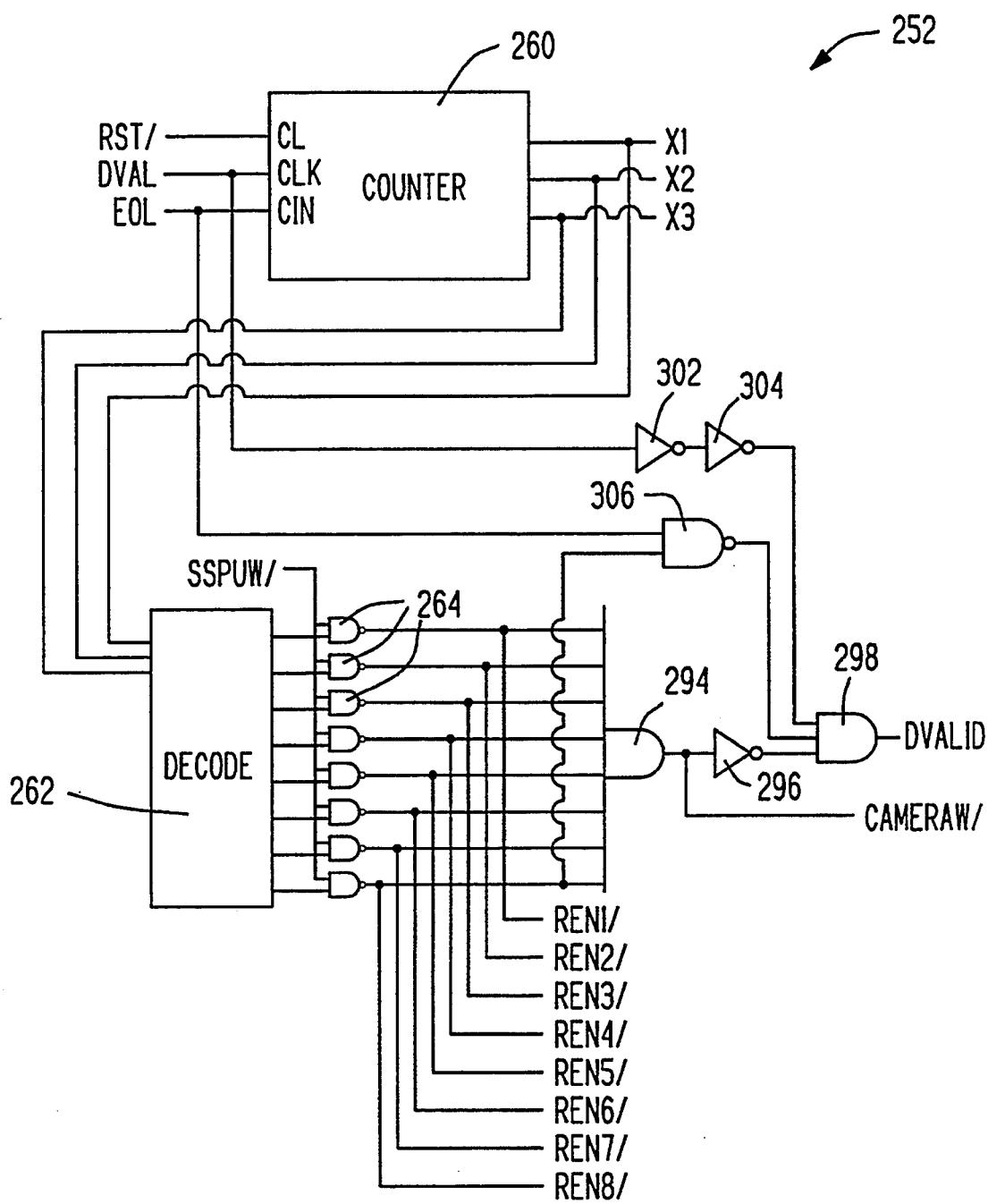
FIG. 9 is a detailed block diagram of circuitry incorporated in a field programmable gate array unit (FPGA) in the circuit of FIG. 8.

In the FPGA 252 as shown in FIG. 9, the outputs X1, X2 and X3 of a counter are decoded by conventional decoding circuitry 262 which through NAND gates 264 enabled when the signal SSPUW/ is high generates a corresponding one of the signals REN1/-REN8/. Referring back to FIG. 6b, the RENX input in each defect detection circuit is connected by a jumper (not shown) to a corresponding one of the eight lines REN1/-RENS/, FIG. 9, to provide for multiplexing the reading of the defect data in the FIFOs 130a and 130b of the eight defect detection circuits. The input RENX/ is applied by inverter 272 to one input of an AND gate 274 which has a second input receiving the master clock signal CLK from the timing circuit 68, FIG. 2. Third and fourth inputs of the AND gate 274 are connected to the line RST/ and the output of the flip-flop 238 to disable reading during resetting of the circuit. The output of the AND gate 274 is passed through a NAND gate 276 to the line R/ to read records from the FIFOs 130a and 130b onto the buses CB and RB/SB until an EOL bit is produced. The second input of the NAND gate 276 is connected to an output of a flip-flop 278 which is normally high due to the strobe signal applied through inverter 280 to the clock input of the flip-flop 278. A FIFO empty signal line EF/ from FIFO 130b is connected by inverter 282 to the clear input of a flip-flop 284 which, in the absence of the empty signal, is held clear to prevent its inverted output from operating the clear input of flip-flop 278. However when EF/ goes low, the flip-flop 284 goes high on the next pulse from NAND gate 276 to clear flip-flop 278 and to disable gate 276 and prevent the reading of empty FIFOs. When EF/ goes high indicating that the FIFOs are not empty, the flip-flop 284 is cleared to remove the clear signal from flip-flop 278 and permit flip-flop 278 to be set high by the next strobe pulse.

The RENX/ signal is also applied by an inverter 286 to an enable input of a tristate buffer 288 which then passes the R/ signal from an inverter 290 to the signal line DVAL which indicates the presence of valid defect data on the CB and RB/SB buses.

The EOL bit from each FIFO 130b is applied to the clock enable input of the counter 260 which is then stepped by the DVAL pulse on its clock input to advance the count in the counter 260. This advances control to the next REN2/- RENS/ control line until the last channel has been read. An AND gate 294 has inputs from all the signals REN1/-RENS/ to produce the CAMERAW/ signal during readout of the defect data uncovered in an image line. An inverter 296 applies the output of the AND gate 294 to one input of an AND gate 298 to enable the gate 298 to pass the signal DVAL through inverters 302 and 304 as the signal DVALID. A third input to the AND gate 298 is received from a NAND gate 306 which has inputs connected to the line RENS/ and to the line EOL to disable the gate 298 during each EOL signal except when the circuit 252 is reading the last defect detection channel in the camera. Thus the records with high EOL bits from the FIFOs are not recognized by the multiplexer and interface unit 38 as being valid data except for the records with EOL signals from the last camera channel and only one record with an EOL bit high is received as valid data by the multiplexer and interface unit 38 for each image line read out of a camera. If an image line analyzed by the camera contains no pixels of a defect, only a single record with an end of line bit high is transmitted from the camera to the multiplexer and interface unit 38.

Each pixel record in the FIFOs 130a and 130b includes on end of line bit (EOL), eight bits of pixel coordinate, and eight bits of pixel intensity. Three additional coordinate bits, identifying the channel in the camera, are added to each data record in transmission to the multiplexer and interface unit 38 to bring the total number of bits to twenty during this transmission. The multiplexer and interface unit 38 adds four more coordinate bits identifying the camera from which the data record is read to increase the record bits to twenty-four total bits transmitted from the unit 38 to the image processing unit 42.

Figure 10:
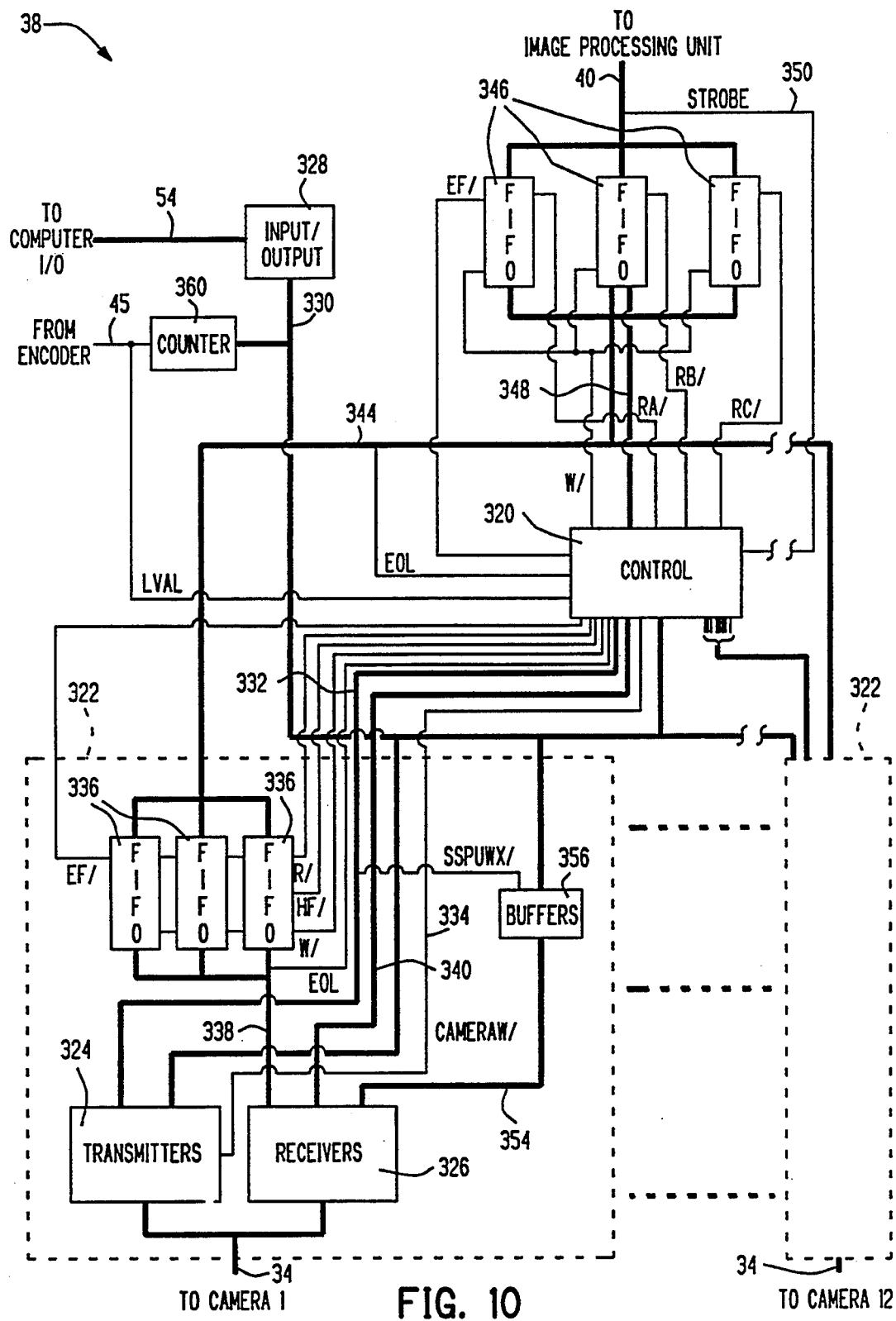
FIG. 10 is a block diagram of circuitry included in a multiplexer and interface unit of FIG. 1.

As illustrated in FIG. 10, the multiplexer and interface unit 38 contains a central control 320 connected by individual control and data lines to a plurality of substantially similar printed circuit units 322 corresponding to the plurality of cameras 30, FIG. 1. Each of the units 322 include RS-422 type transmitters 322 and receivers 324 connected to appropriate lines in the corresponding cable 34. The system is under the general control of the computer 46, FIG. 1, through the bus 54 connected to input/output circuit 328. Bus 330 connected to the circuit 328 includes RST/ and RESTART/ lines (not shown) connected to control 320 as well as to each of the units 322; a RST/ signal resets the entire system while a RESTART/ signal clears the alarm flags caused by the HF/ signals from the FIFOs. The bus 330 also includes PHIL, MWL, TINITL and DEFOVRD lines (not shown) along with camera address lines P0-P3 (not shown) connected to the control circuit 320. Buses 332 each including PHIL, MWL, TINITL and DEFOVRD lines (not shown) are connected from the control circuit 320 to the transmitters in the respective units 322. The bus 330 further contains eight SB data lines (not shown) which are connected to transmitters in block 324 controlled by a CAMERAWX/ signal on line 334 from the control circuit 320. In response to a PHIL, MWL, TINITL or DEFOVRD signal over bus 330 from the computer, the control unit 320 sends the corresponding PHIL, MWL, TINITL or DEFOVRD over the bus 332 to the unit 322 addressed by the signals P0-P3 so as to enable the computer to set the values in latches 140, 142 and 144, FIG. 6a, in the selected cameras to the values SB on the system bus 146.

Each of the units 322 includes three FIFOs 336 to which the twenty incoming data lines in bus 338 from receivers 326 are connected for receiving and temporarily storing the defect data records from the corresponding camera including an EOL flag bit, eight pixel intensity value bits RB and eleven X-coordinate bits CB. A bus 340 including DVALID, CAMERAWX/ and ALARM lines (not shown) is connected from the receivers 326 to the control circuit 320 which in response to the DVALID and CAMERAWX/ signals applies write signals to a line W/ to stored each incoming record in the FIFOs 336. The control circuit also contains circuitry, similar to that of FIG. 6b, connected to a line HF/ from the FIFOs 336 for blocking the write signals, except when a signal is on the line EOL, in response to the FIFOs becoming half full to indicate excessive defects being detected by the corresponding camera. Production of write signals can be restarted by a RESTART/ or a RST/ signal from the computer.

Data outputs of the FIFOs 336 in all the units 322 are connected to a common twenty line bus 344 to inputs of FIFOs 346 which have four additional inputs connected to a bus 348 from the control unit 320 carrying camera address signals. In response to the absence of an EF/ or empty signal from the FIFOs 336, the control unit 320 generates read signals R/ applied to the FIFOs 336 in one selected unit 322 to output defect data records from that selected unit 322 until a record contains an EOL flag. Simultaneously, the control unit 320 generates write signals on a line W/ to the FIFOs 346 to store the records being read from the selected unit 322 into the FIFOs 346. The control unit 320 contains circuitry similar to FIG. 9 responsive to the EOL signal on bus 344 for suppressing the write signal W/ to FIFOs 346, except when the twelfth unit 322 is being read. Thus records of defects in each image line extending across the view of all twelve cameras are assembled in the FIFOs 246 with an end record having the EOL bit flag from the twelfth camera. If an image line across the web being viewed contains no defects, only a single record from the twelfth camera with an EOL flag is placed in the FIFOs 346.

The twenty-four-bit records assembled in the FIFOs 346 are transferred over the bus 40 to image processing unit 42 in eight-bit sequential bytes since the image processing unit 42, such as and OCULUS 500 MS board, can only receive data words having eight bits. The control unit 320 in response to absence of an empty signal EF/ from the FIFOs 346 sequentially applies read signals RA/, RB/ and RC/ to the respective FIFOs 346 to sequential apply the outputs of these FIFOs to the bus 40. The control unit also generates a strobe signal on line 350 of the bus 40 during each read signal RA/ , RB/ and RC/ to store the record in the unit 42.

Two additional control lines in the bus 330 carry signals to the control unit 320 for causing the generation of SSPUW/ signals on a line (not shown) in each of the buses 332. One of these control signals causes the control unit to send the SSPUW/ signals to all the cameras at the same time; this is needed to enable data to be sent to the system bus 146 during the PHIL, MWL or TINITL signals. The second of these control signals enables a counting and decoding circuit (not shown) for sequentially generating and applying SSPUW/ signals to the buses 332 in the units 322. This counting circuit is stepped to the count of twelve by the LVAL signal from the encoder 44. During each SSPUW/ signal, the signals ALARM1/-ALARM8/ from the camera channels are applied through a bus 354 and tristate buffers 356 to the bus 330 so that the computer can read the alarm status of the eight channels in each of the cameras. The computer can periodically generate RESTART/ signals and later read the alarm status of the camera channels to monitor the edges of the web. A more precise determination of the edge position can be made by analyzing the defect pixel data generated immediately after a RESTART/ signal and before the edge channels shut down. During the SSPUW/ signal, transmission of defect data records from the corresponding camera are disabled, and generally records corresponding to one image line are lost. Cycling through all twelve cameras substantially insures that the records being collected by each of the units 322 generally lose the same number of lines so that the records read during one cycle from the units 322 relate to a single image line or adjacent image lines on the web.

The camera alarm signal ALARM in each bus 340 is ORed with the HF/ signal from the corresponding FIFOs 336 by the control unit 320. These ORed alarm signals are also made available for being read over bus 330 by the computer so that the computer can easily monitor the alarm status. Normally only the extreme edge cameras, cameras one and twelve, will generate alarm signals, and if one of the other cameras generate an alarm, the computer can readily determine the cause of the alarm.

A counter 360 is included in the circuit of FIG. 10 for counting the encoder pulses LVAL. The count is made available to the computer over the bus 330 so that the computer can compare the count of counter 360 with the count made by the image processing unit 42 from records with EOL flags.

In the image processing unit 42, the records being inputted over bus 40 are monitored for defects. EOL records are used to maintain a line count which indicates the Y-position or coordinate of the image line corresponding to the record. If defect records are uncovered, those with adjacent X-coordinates are assembled and placed in a proper relative address in a video buffer in the processing unit 42 so that the monitor displays the defect. Also the assembled defect data with corresponding X and Y coordinates is transferred to memory common with the computer 46 so that the computer can use the Guay algorithms to identify the type of defect and make a record which can then be printed in a conventional manner.

Since many modifications, variations, and changes in detail may be made to the above described embodiment, it is intended that the foregoing description and the accompanying drawings be interpreted as only illustrative and not in a limiting sense.

What is claimed is:

1. A defect detection system comprising a camera housing;
    an array sensor having a plurality of outputs mounted in the camera housing;
    a lens mounted on the camera housing for projecting an image of an object under test onto the array sensor;
    means for operating the array sensor to generate video signals from the respective outputs representing respective sections of the image of the object;
    a coordinate counter for generating a coordinate for pixels in the video signals from the outputs;
    means mounted in the camera housing for detecting pixels in the video signal of a defect in the object from each of the outputs;
    a section counter for generating a plurality of bits identifying the image section containing each of the detected defect pixels; and
    camera output means mounted in the camera housing for transmitting out of the camera housing to a remote image processing unit:
        the detected defect pixels apart from normal pixels in the video signal from each of the outputs whereby the quantity of pixel values transmitted by the camera output means is less than the quantity of pixel values in the video signal,
        the coordinate for each of the detected defect pixels, and
        the plurality of bits identifying the image section containing each of the detected defect pixels.

2. A defect detection system as claimed in claim 1 wherein the camera output means includes means for temporarily storing the detected defect pixels prior to transmitting the detected defect pixels.

3. A defect detection system as claimed in claim 2 wherein the temporary storing means includes a first-in first-out memory.

4. A defect detection system as claimed in claim 1 wherein the means for detecting defect pixels in the video signal includes means for determining if each pixel in the video signal is within an acceptable range of pixel values.

5. A defect detection system as claimed in claim 4 including means responsive to a change in pixels within the acceptable range of pixel values for changing the acceptable range of pixel values so that the acceptable range of pixels values follows gradual changes in the pixels of the video signal.

6. A defect detection system as claimed in claim 4 wherein the means for determining if each pixel is within the acceptable range includes
    a subtraction circuit receiving a value of each present pixel and a prior pixel value derived from at least one prior pixel for producing a difference between the present pixel value and the prior pixel value, and
    a comparison circuit receiving the difference from the subtraction circuit for producing a defect signal if the difference exceeds a predetermined value.

7. A defect detection system as claimed in claim 6 including means for temporarily storing the prior pixel value derived from at least one prior pixel and presenting the stored prior pixel value to the subtraction circuit, means responsive to the absence of the defect signal for updating the stored prior pixel value to in accordance with a succeeding prior pixel value derived from at least one prior pixel value, and means responsive to the defect signal for maintaining the stored prior pixel value at its present value.

8. A defect detection system as claimed in claim 1 further comprising means mounted in the camera housing and responsive to receipt of an external control signal for overriding the defect pixel detecting means and for operating the camera output means to transmit both normal and defect pixels from the video signal.

9. A defect detection system as claimed in claim 2 further comprising analog to digital converter means mounted in the camera housing for converting pixels in the video signals from the array sensor into multi-bit digital pixel values; and wherein the defect detecting means receives the multi-bit digital pixel values and determines defect pixels from the multi-bit digital pixel values, and the defect pixel storing means stores multi-bit digital defect pixel values.

10. A defect detection system comprising
    a camera housing;
    a TDI CCD two-dimensional array sensor mounted in the camera housing and having a plurality of outputs each for generating a video signal of a corresponding section of an image of a moving object;
    a lens mounted on the housing for projecting the image of the moving object onto the array sensor;
    a plurality of defect detecting circuits mounted in the camera housing and being connected to the respective plurality of outputs of the array sensor;
    a coordinate counter for generating a coordinate for pixels in the video signals from the outputs;
    a plurality of temporary memories mounted in the camera housing for storing defect pixel values detected by the respective plurality of defect detecting circuits and the coordinate for each of the detected defect pixel values;
    a section counter for generating a plurality of bits identifying the image section containing each of the detected defect pixels; and
    camera output means mounted in the camera housing for reading the temporary memories and transferring out of the camera housing to a remote image processing unit the stored defect pixel values and the stored coordinates along with the image section identifying bits.

11. A defect detection system as claimed in claim 10 wherein the output means sequentially reads the temporary memories to sequentially transfer the defect pixel values.

12. A defect detection system as claimed in claim 10 wherein each temporary memory includes means for storing an end of line signal; and the output means includes means for sequentially selecting reading the plurality of temporary memories to read the memories, and means responsive to an end of line signal from a temporary memory for selecting the next temporary memory.

13. A defect detection system as claimed in claim 12 wherein the sequential selecting means includes a counter for counting the end of line signals.

14. A defect detection system as claimed in claim 10 further comprising means mounted in the camera housing and responsive to receipt of an external control signal for overriding the plurality of defect pixel detecting circuits and for operating the plurality of memories to store both normal and defect pixels from the respective video signals of the outputs of the array sensor.

15. A defect detection system as claimed in claim 10 further comprising a plurality of analog to digital converter means mounted in the camera housing for converting pixels in the respective video signals from the outputs of the array sensor into respective streams of multi-bit digital pixel values; and wherein the plurality of defect detecting circuits receive the respective streams of multi-bit digital pixel values and determine defect pixels from the multi-bit digital pixel values, and the plurality of memories store the detected multi-bit digital defect pixel values from the respective streams.

16. A defect detection system comprising:
a camera housing;
a CCD array sensor mounted in the camera housing and having a plurality of outputs each for generating a video signal of a corresponding section of an image of a moving object;
a lens mounted on the housing for projecting the image of the moving object onto the array sensor;
a plurality of defect detecting circuits mounted in the camera housing and being connected to the respective plurality of outputs of the array sensor;
a plurality of temporary memories mounted in the camera housing for storing defect pixel values detected by the respective plurality of defect detecting circuits, each temporary memory including means for storing a coordinate for each detected defect pixel value and means for storing an end of line signal; and
camera output means mounted in the camera housing for reading the temporary memories and including a counter for counting the end of line signals to sequentially select the plurality of temporary memories, means for reading the coordinates along with the defect pixel values, means for incorporating the output of the counter into the coordinates, and means for transferring the coordinates with the incorporated counter output along with the detected defect pixel values.

17. A defect detection system comprising
an array sensor for generating successive pixel values of an image portion of a moving object, the array sensor having a plurality of outputs, each of the outputs for generating successive pixel values of a corresponding section of an image of a moving object;
a plurality of defect detecting circuits, each of the defect detecting circuits connected to a corresponding one of the outputs of the array sensor for detecting defective pixel values in the pixel values of the corresponding section of the image portion;
a coordinate counter for generating a coordinate for pixels in the video signals from the outputs;
a temporary memory corresponding to each of the defect detecting circuits;
means responsive to each defect detecting circuit detecting defective pixel values for storing the defective pixel values and the coordinate for each of the detected defective pixel values in the corresponding temporary memory;
a section counter for generating a plurality of bits identifying the image section containing defect pixels corresponding to the detected defective pixel values;

means for reading the temporary memories and transmitting out of the camera housing to a remote image processing unit the stored defective pixel values and the stored coordinates from each of the temporary memories along with the corresponding plurality of image section identifying bits at a rate which is less than the rate at which the array sensor generates the pixel values; and
means for determining the presence of more than a predetermined number of unread stored defective pixel values in each of the temporary memories to disable the corresponding defective pixel value storing means.

18. A defect detecting system as claimed in claim 17 wherein the array sensor generates successive pixel values of each of a plurality of image lines of the image portion, the system includes means for storing an end of line flag in the temporary memory for each image line sensed by the sensor irrespective of the number of unread stored defective pixel values, and the reading out means reads out each stored end of line flag after reading out any stored defective pixels corresponding to each end of line flag.

19. A defect detecting system as claimed in claim 18 wherein the section counter is responsive to the end of line flag reading out means.

20. A defect detection system as claimed in claim 17 wherein the means for determining the presence of more than a predetermined number of unread stored defective pixel values includes means for maintaining the defective pixel storing means disabled after the reading out means reduces the number of unread stored defective pixel values to less than the predetermined number.

21. A defect detecting system as claimed in claim 17 wherein each temporary memory is a first-in, first-out memory having a half-full flag, and the means for determining the presence of more than a predetermined number of unread stored defective pixel values responds to the half-full flag to determine the presence of more than the predetermined number.

22. A defect detection system as claimed in claim 17 wherein each output of the array sensor generates successive pixel values of each of a plurality of image lines of the corresponding image section; and the system includes a plurality of means for storing end of line flags in the respective memories for each image line of the respective sections irrespective of the number of unread stored defective pixel values, and the reading out means reads out each stored end of line flag after reading out any stored defective pixels of an image line corresponding to each end of line flag and sequences to the reading out of the next memory in response to each end of line flag.

23. A defect detection system as claimed in claim 17 including means for determining an edge of the object by sensing which of the plurality of means for determining the presence of more than a predetermined number of unread stored defective pixel values in the respective memories have operated disabled the respective defective pixel value storing means.

24. A defect detection system as claimed in claim 17 further comprising means mounted in the camera housing and responsive to receipt of an external control signal for overriding the defect pixel detecting means and for operating the defect pixel storing means to store both normal and defect pixels from the video signal.

25. A defect detection system comprising a TDI CCD two-dimensional array sensor having a plurality of outputs each for generating successive pixel values of a corresponding section of an image of a moving object, each output of the array sensor generating successive pixel values of each of a plurality of image lines of the corresponding image section;

a plurality of defect detecting circuits connected to the respective plurality of outputs of the array sensor for detecting defective pixel values in the pixel values from the respective outputs;

a plurality of temporary memories corresponding to the plurality of detecting means;

a plurality of means responsive to the respective defect detecting circuits for storing the defective pixel values in the respective temporary memories;

a plurality of means for storing end of line flags in the respective memories for each image line of the respective sections;

means for reading out stored defective pixel values from the plurality of memories one memory at a time at a rate which is less than the rate at which the array sensor generates the pixel values;

said reading out means also reading out each stored end of line flag after reading out any stored defective pixels of an image line corresponding to each end of line flag and sequencing to the reading out of the next memory in response to each end of line flag;

a plurality of means for determining the presence of more than a predetermined number of unread stored defective pixel values in the respective memories to disable the respective defective pixel value storing means;

said plurality of end of line flag storing means storing end of line flags in the respective memories for each image line of the respective sections irrespective of the number of unread stored defective pixel values; and wherein the reading out means includes means for discarding the end of line flags from all but one designated memory of the plurality of memories so that all defect pixels on a common line through the image sections are sequentially outputted with a single end of line flag.

* * * * *